United States Patent [19]

Fanta et al.

[11] 4,045,469
[45] Aug. 30, 1977

[54] INSECTICIDAL ESTERS OF SPIRO CARBOXYLIC ACIDS

[75] Inventors: Wayne I. Fanta, Colerain Township, Hamilton County; Joel I. Shulman, Springfield Township, Hamilton County, both of Ohio

[73] Assignee: The Procter & Gamble Company, Cincinnati, Ohio

[21] Appl. No.: 360,864

[22] Filed: May 16, 1973

Related U.S. Application Data

[62] Division of Ser. No. 157,033, June 25, 1971, Pat. No. 3,823,177.

[51] Int. Cl.² .................. C07C 69/76; C07C 63/337; C07C 63/44
[52] U.S. Cl. .............................. 260/469; 260/515 R
[58] Field of Search .......................... 260/469, 515 R

[56] References Cited

U.S. PATENT DOCUMENTS

| 3,419,604 | 12/1968 | Kaiser et al. | 260/501.1 |
| 3,636,059 | 1/1972 | Matsui et al. | 260/347.4 |
| 3,720,703 | 3/1973 | Elliott et al. | 260/468 H |

FOREIGN PATENT DOCUMENTS 1,207,371  9/1970  United Kingdom

*Primary Examiner*—Lorraine A. Weinberger
*Assistant Examiner*—Michael Shippen
*Attorney, Agent, or Firm*—Rose Ann Dabek; Jerry J. Yetter; Richard C. Witte

[57] ABSTRACT

Described are certain spiro carboxylic acids and their allethrolone esters. The esters of these acids possess unique insecticidal properties and are useful as such in home, garden and agricultural applications.

5 Claims, No Drawings

INSECTICIDAL ESTERS OF SPIRO CARBOXYLIC ACIDS

This is a division of application Ser. No. 157,033, filed June 25, 1971, now U.S. Pat. No. 3,823,177.

BACKGROUND OF THE INVENTION

This invention relates to novel spiro carboxylic acids and their insecticidal esters, as well as insecticidal compositions containing said esters as an essential active ingredient.

Current trends in the chemical control of insects call for inherently safer materials which degrade very rapidly to non-toxic substances once their purpose is accomplished. The safety of the widely used chlorinated hydrocarbons, notably DDT, is currently under question largely because of their poor biodegradability and concomitant persistence. Accordingly, there is a great demand for alternative broad spectrum insecticides which are suitable for the high volume usage entailed in agricultural applications. At the same time it is desirable for new insecticides to exhibit a low order of toxicity to warm-blooded animals. Of the several insecticide classes which demonstrate low mammalian toxicity and good biodegradability, it has long been recognized that pyrethrum, a naturally-occurring insecticidal mixture, possesses these desirable properties. In addition to the safety advantages, this natural mixture causes rapid knockdown and kill of a broad spectrum of insects; however, it is unstable to light, air, and heat, and is very expensive. The most active component of pyrethrum is pyrethrin I and a number of analogous compounds have been proposed for insecticidal use. Allethrin, a typical synthetic pyrethrin-like insecticide, while more stable to light and heat than pyrethrum, is nevertheless expensive, a defect which is compounded by the fact that this substance is not appreciably synergized by the low cost synergizing agents such as piperonyl butoxide which are typically used in insecticidal compositions. Because of instability, high cost and limited supply, the use of pyrethrum and pyrethrin-like insecticides in agricultural applications has been precluded or seriously limited.

At the same time, it is well known that certain insects, in time, become immune to the insecticidal properties of various chemical agents. To be efficient, an insecticide should be able to resist detoxification by the insect. The biological mechanisms whereby insects are capable of detoxifying the various types of insecticidal compounds are not known. However, it has been suggested that with compounds which are analogous to pyrethrin, e.g., allethrin, one mode of detoxification may involve oxidation of one or both of the methyl groups on the isobut-1-enyl side chain of the chrysanthemic acid moiety present in that compound. Additionally, it is possible that, as with other biological systems, insects may in time develop new biogenetic mechanisms capable of detoxifying any particular insecticidal compound. In any event, it is desirable to have included in the insecticidal armamentarium compounds which may be utilized once a given class of insects is found no longer to respond to conventional insecticidal compounds.

Many prior art insecticidal esters differ from one another and from the natural pyrethrin I esters by virtue of synthetic modifications in the alcohol moiety of the ester. Other synthetic insecticides are pyrethrin-like esters modified in the acid portion of the ester molecule. British specification No. 1,207,371, Sept. 3, 1970, relates to the allethrolone esters of the spiro carboxylic acids 2-(isobut-1'-enyl) spiro[2.5]octane-1-carboxylic acid and 2-(isobut-1'-enyl) spiro[2.4]heptane-1-carboxylic acid. French Patent 1,505,423, December, 1967, relates to the ethyl and allethrolone esters of 2,2,5-trimethylspiro [2.5]oct-4-ene-1-carboxylic acid. By the present invention, certain novel spiro carboxylic acids are provided which, when esterified with various alcohols, form insecticidal analogues of pyrethrin which are modified in the acid moiety of the ester. Suprisingly, the allethrolone esters of the acids herein exhibit miticidal activity, a property not shared by many other pyrethrin-like compounds.

It is therefore an object of this invention to provide novel spiro carboxylic acids which can be esterified to provide a variety of insecticidal compounds which are biodegradable, effect rapid knock-down and kill of a broad spectrum of insects (the term "insects" herein includes mites, and the term "insecticidal" includes miticidal) possess low mammalian toxicity, and are less susceptible to detoxification by insects that is pyrethrum. It is a further object of this invention to provide certain insecticidal allethrolone esters of novel spiro carboxylic acids. These and other objects are obtained by the present invention as will become apparent from the following disclosure.

SUMMARY OF THE INVENTION

The novel compounds of the present invention include 2,2-dimethylspiro[2.4]hepta-4,6-diene-1-carboxylic acid and certain acids related thereto, as well as the allethrolone esters of said spiro carboxylic acids.

This invention also encompasses insecticidal compositions comprising as an essential ingredient, an insecticidal amount of a compound selected from the group consisting of the allethrolone esters of 2,2-dimethylspiro[2.4]hepta-4,6-diene-1-carboxylic acid, and acids related thereto, as hereinafter detailed, and a carrier.

DETAILED DESCRIPTION OF THE INVENTION

The novel acids of this invention are the following:

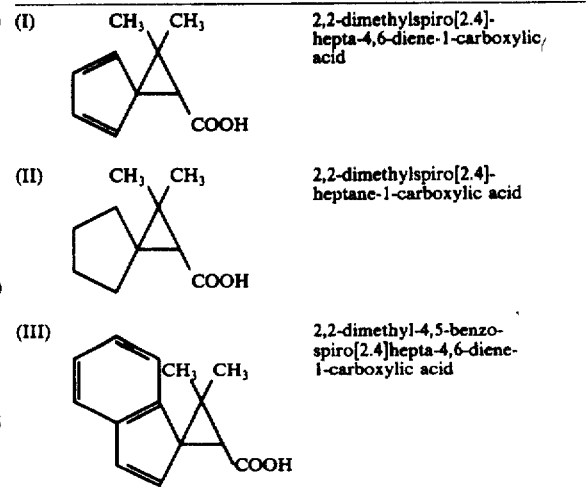

(I) 2,2-dimethylspiro[2.4]hepta-4,6-diene-1-carboxylic acid (II) 2,2-dimethylspiro[2.4]heptane-1-carboxylic acid (III) 2,2-dimethyl-4,5-benzo-spiro[2.4]hepta-4,6-diene-1-carboxylic acid

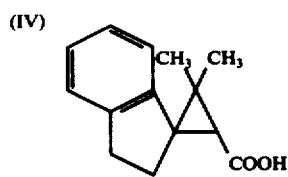

(IV) 2,2-dimethyl-4,5-benzo-spiro[2.4]hepta-4-ene-1-carboxylic acid

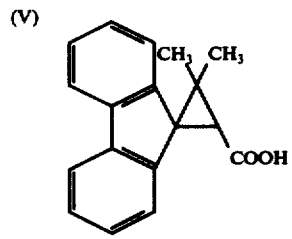

(V) 2,2-dimethyl-4,5,6,7-dibenzospiro-[2.4]hepta-4,6-diene-1-carboxylic acid

The novel insecticidal allethrolone esters of acids (I) through (V), above, are the following:

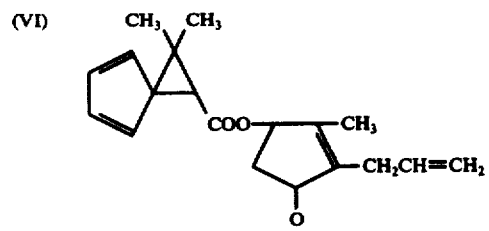

(VI)

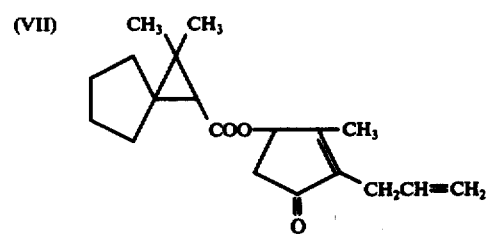

(VII)

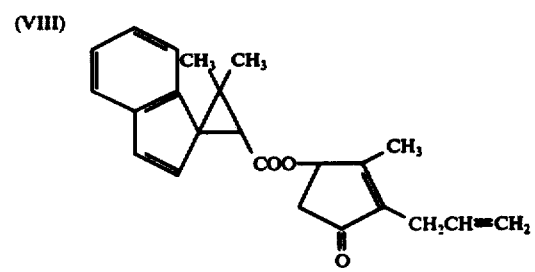

(VIII)

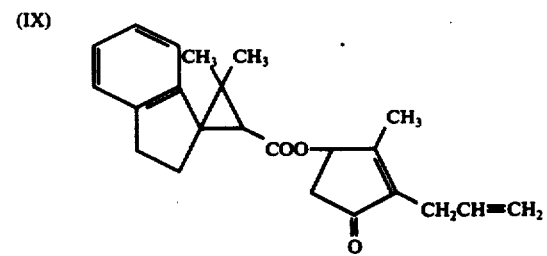

(IX)

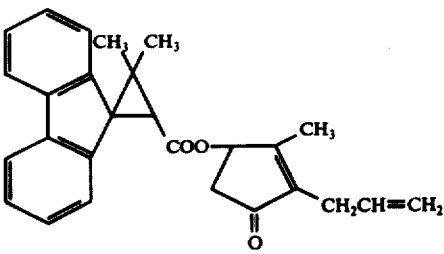

(X)

The preparation of the foregoing acids, (I) through (V) and their corresponding allethrolone esters, is fully disclosed by the following examples. In each instance the alkyl ester of the spiro carboxylic acid is first prepared and then hydrolyzed to the free acid. The acids are then converted to the acid halide form and esterified with allethrolone, which can be synthesized by methods well known in the art.

EXAMPLE I

Compound I;
2,2-Dimethylspiro[2.4]hepta-4,6-diene-1-carboxylic Acid

6,6-Dimethylfulvene

A 0° C mixture of 58 g. of cyclopentadiene monomer and 51 g. of acetone was treated with 15 g. of 40% aqueous methylamine as described by Freiesleben, German Auslegeschrift No. 1,146,050 (1963); Chem. Abstr., 59, 9914 (1963). The mixture was stirred at room temperature for 0.5 hr. during which time 24 ml. of water separated. The reaction was stirred for an additional 0.5 hr. (4 ml. water additional) and placed in a refrigerator for 19 hr. (8 ml. water additional). The total was dried over MgSO$_4$ and distilled to afford 58 g. (62%) of dimethylfulvene: b.p. 35–38° C (4.5 mm.); ir (neat) 6.08, 6.17, 7.30, 9.18, 11.6, 13.0 μ.

Ethyl 2,2-Dimethylspiro[2.4]hepta-4,6-diene-1-carboxylate

A well stirred, 10°–15° C nitrogen blanketed mixture of 10.6 g. of 6,6-dimethylfulvene, prepared above, and 12.2 g. of ethyl chloroacetate was treated dropwise over 1.5 hr. with a solution of 11.7 g. of potassium t-butoxide in 75 ml. of dry t-butyl alcohol. The reaction was stirred an additional 1.5 hr. at 10° C and most of the alcohol was then removed at reduced pressure. Ether extraction of an aqueous solution of the residual semisolid afforded 15.2 g. of yellow oil. Subsequent distillation afforded 2.5 g. (13%) of yellow ester, b.p. 75°–80° C (0.25 mm.). Gas chromatographically purified ester exhibited the following spectral properties: ir (film) 5.77, 8.33, 8.69, 9.24, 12.0, 12.7 μ; nmr (CCl$_4$) τ 3.38, 3.69, 3.99 (3m, 4, —C$\underline{H}$=C$\underline{H}$—C$\underline{H}$=C$\underline{H}$—), 5.99 (q, 2, J = 7 Hz, OC$\underline{H}_2$CH$_3$), 7.41 (s, 1, C$\underline{H}$CO$_2$Et), 8.47, 8.60 (6, C$\underline{H}_3$'s), 8.80 (t, 3, J = 7 Hz, OCH$_2$C$\underline{H}_3$).

2,2-Dimethylspiro[2.4]hepta-4,6-diene-1-carboxylic Acid (Compound I)

A solution of 2.5 g. of the ester prepared above in 15 ml. of ethanol was saponified by heating with a solution of 7.4 g. of potassium hydroxide in 70 ml. of water. Work-up afforded 2 g. (93%) of crystalline acid which on recrystallization from ether afforded 1.63 g.: m.p. 126°–129° C; ir (CHCl$_3$) 5.87, 7.63, 7.94, 8.98, 10.2, 11.5

μ; nmr (CDCl$_3$) τ -1.94 (s, 1, O$\underline{H}$), 3.32, 3.58, 3.89 (3m, 4, —C$\underline{H}$=CH—C$\underline{H}$=CH—), 7.30 (s, 1, C$\underline{H}$CO$_2$H), 8.44, 8.59 (2s, 6, CH$_3$'s). This data corresponds to that for a compound of the structure assigned to Compound (I), above.

Comppound VI; Allethrolone Ester of 2,2-Dimethylspiro-[2.4]hepta-4,6-diene-1-carboxylic Acid 2,2-Dimethylspiro[2.4]hepta-4,6-diene-1-carboxylic Acid Chloride A solution of 1.33 g. of the parent acid (I) in 10 ml. of hexane was converted to the acid chloride by refluxing with excess SOCl$_2$ in hexane for 5 hours. Distillation yielded 0.8 g. (54%) of yellow acid chloride: b.p. ~ 80° C (1 mm.); ir (neat) 5.60, 9.64, 12.1, 13.2 μ; nmr (CCl$_4$) τ 3.5 (m, 3) and 3.9 (m, 1, C$\underline{H}$=CH—C$\underline{H}$=CH), 6.8 (s, 1, C$\underline{H}$COCl), 8.4, 8.5 (2s, 6, CH$_3$'s).

Esterification

A mixture of 0.8 g. of the acid chloride prepared above in 15 ml. of benzene and 0.7 g. of pyridine was treated with 0.67 g. of allethrolone at 0° C, thence rising to room temperature over a 24 hour period. The crude ester product (92%) was chromatographed on Florisil to afford 0.76 g. of pure ester. Material purified by gas chromatography exhibited the following spectral properties: ir (neat) 5.76, 5.82, 6.02, 6.09, 8.39, 8.72, 9.23, 12.7 μ; nmr (CCl$_4$) τ 3.42, 3.65, 3.96 (3m, 4, —C$\underline{H}$=CH—CH=CH—), 4.38 (m, 2, —C$\underline{H}$=CH$_2$, C$\underline{H}$—O—), 5.13 (m, 2, —CH=C$\underline{H}_2$), 7.14 (d, 2, J = 6 Hz, —C$\underline{H}_2$—CH=), 7.35 (s, 1, C$\underline{H}$CO$_2$—), 8.03 (s, CH=CC$\underline{H}_3$), 8.46, 8.59 (2s, 6, CH$_3$'s). This data corresponds to that for a compound of the structure assigned to Compound (VI), above.

EXAMPLE II

Compound II; 2,2-Dimethylspiro[2.4]heptane-1-carboxylic Acid

Ethyl 2,2-Dimethylspiro[2.4]heptane-1-carboxylate

A solution of 1.54 g. of ethyl 2,2-dimethylspiro[2.4]-hepta-4,6-diene-1 carboxylate prepared in Example I, above, in 30 ml. of ethanol was catalytically reduced over 50 mg. of pre-reduced platinum oxide. The theoretical amount of hydrogen was taken up over a 3 hr. period. The catalyst was removed by filtration and the alcohol was removed at reduced pressure. The residue, 1.5 g. (100%) could be used directly without further purification.

Material purified by glpc exhibited the following spectral properties: ir (film) 5.78, 7.46, 8.49, 8.79, 9.44, 11.8 μ; nmr (CCl$_4$) τ 6.02 (q, 2, J = 7 Hz, OCH$_2$CH$_3$), 8.79 (t, 3, J = 7 Hz, OCH$_2$CH$_3$), 8.83, 8.86 [2s, 6, C(CH$_3$)$_2$]; $n_D^{27}$ 1.4591. Anal. Calc'd. for C$_{12}$H$_{20}$O$_2$: C, 73.43; H, 10.27. Found: C, 73.9; H, 10.4.

2,2-Dimethylspiro[2.4]heptane-1-carboxylic acid (Compound II)

A solution of 3.3 g. of crude spiro ester (prepared above) in 70 ml. of ethanol was treated with a solution of 9.45 g. of potassium hydroxide in 15 ml. of water. The resulting reaction mixture was heated at 50° C for 24 hr. The cooled reaction mixture was saturated with salt and extracted well with ether. The basic aqueous solution was acidified with cold dilute acid and the acidic material was isolated with ether. Removal of the dried (MgSO$_4$) solvent afforded 2.9 g. (100%) of crude, crystalline acid which could be used directly without further purification. Material purified by preparative glpc exhibited the following properties: m.p. 68°–70° C; ir (KBr) 3.1–4.0, 5.95, μ; nmr (CDCl$_3$) τ 8.33 (m, 8, —(C$\underline{H}_2$)$_4$—), 8.75 (s, 1, —C$\underline{H}$CO$_2$H), 8.78 [2s, 6, C(C$\underline{H}_3$)$_2$]. Anal. Calc'd. for C$_{10}$H$_{16}$O$_2$: C, 71.39; H, 9.59. Found: C, 71.3; H, 9.6. This data corresponds to that for a compound of the structure assigned to Compound (II), above.

Compound VII; Allethrolone Ester of 2,2-Dimethylspiro-[2.4]heptane-1-carboxylic Acid 2,2-Dimethylspiro[2.4]heptane-1-carboxylic acid chloride.

A solution of 3 g. of crude acid (II), above, and 2.7 g. of thionyl chloride in 30 ml. of hexane was refluxed for 5 hr. The volatile materials were removed at reduced pressure and the acid chloride product was distilled to afford 2.35 g. (75%): b.p. 63° C (0.2 mm.); ir (film) 5.59, 9.02, 9.45, 9.99, 12.02, 13.20 μ.

Esterification

A solution of 2.35 g. of the parent acid chloride (above) in 20 ml. of benzene was treated with 2 g. of pyridine, cooled in an ice bath and treated with a solution of 1.93 g. of allethrolone in 20 ml. of benzene. The resulting solution was stirred at room temperature for 24 hours. The reaction mixture was added to brine solution and extracted with ether. The combined ether extracts were washed with 5% aqueous, hydrochloric acid, 0.1 N aqueous sodium hydroxide, and brine. Drying (MgSO$_4$) and solvent removal afforded crude product which was subsequently distilled to afford 3.32 g. (87%) of oily ester; b.p. 125°–130° C (0.02 mm.). Material purified by glpc exhibited the following spectral properties: ir (film) 5.79, 5.82, 8.62, 8.78, 8.94, 9.49 μ; nmr (CCl$_4$) τ 4.20–4.55 (2m's, 2, —OC$\underline{H}$<, C$\underline{H}$=CH$_2$), 4.90-5.21 (m, 2, CH=C$\underline{H}_2$), 8.03 (s, 3, C=CC$\underline{H}_3$), 8.80, 8.82 [2s's, 6, C(CH$_3$)$_2$]. This data corresponds to that for a compound of the structure assigned to Compound (VII), above.

EXAMPLE III

Compound III; 2,2-Dimethyl-4,5-benzospiro[2.4]hepta-4,6-diene-1-carboxylic Acid

Ethyl 2,2-Dimethyl-4,5-benzospiro[2.4]hepta-4,6-diene-1-carboxylate.

A dry 100 ml. three-necked round-bottom flask fitted with a reflux condenser and a pressure equilizing addition funnel was flushed with argon and charged with 7.40 g. of ethyl (dimethylsulfuranylidene)acetate, prepared in the manner of G. B. Payne, J. Org. Chem., 32, 3351 (1967), and 30 ml. of dry methylene chloride. The stirring solution was brought to reflux under an argon atmosphere and a solution of 6,6-dimethyl-1,2-benzofulvene in 15 ml. of dry methylene chloride was added over a period of 15 min. The solution was heated at reflux for 30 min. after the addition was complete, then stirred at 25° C for 17 hr. Concentration (rotary evaporator) and fractional distillation afforded the product as a viscous yellow oil (8.00 g., 66%), boiling range 105°–133° C (0.10 mm.). Gas chromatography showed the product to consist of the two epimers in approximately equal amounts. The product displayed ir bands (neat film) at 5.78 μ (C=O) and 8.60 μ (ester). The nmr spectrum (CDCl$_3$) verified the presence of both possible epimers: ρ 2.1 to 3.3 (complex m, 5.5 H, aromatic as well as both olefinic protons of one epimer and one olefinic proton of the other), 3.77 (d, J = 6 Hz, part of AB quartet, 0.5 H, C<u>H</u>=CH of one epimer), 5.88 (q, J = 7 Hz, 1 H, CH<sub>3</sub>C<u>H</u><sub>2</sub>— on one epimer), 5.93 (q, J = 7 Hz, 1 H, CH<sub>3</sub>C<u>H</u><sub>2</sub>— on the other epimer), 7.33 (s, 1 H, <u>H</u>C—COO— on both epimers), 8.39 and 8.50 (pair of s, total 3 H, gem CH<sub>3</sub> on one epimer), 8.30 and 8.54 (pair of s, total 3 H, gem CH<sub>3</sub> on the other epimer), 8.79 (t, J = 7 Hz, 1.5 H, C<u>H</u><sub>3</sub>CH<sub>2</sub>— on one epimer), and 8.87 (t, J = 7Hz, 1.5 H, C<u>H</u><sub>3</sub>CH<sub>2</sub>— on the other epimer). The ester had molecular ion m/e 242.130 (calc'd. for $C_{16}H_{18}O_2$, 242.1302).

2,2-Dimethyl-4,5-benzospiro[2.4]hepta-4,6-diene-1-carboxylic Acid (Compound III)

To a solution of 3.63 g. of the ethyl ester prepared above in 10ml. of ethanol was added a solution of 3.36 g. of potassium hydroxide in 15 ml. of water. The mixture was heated at reflux for 2.5 hr. then stirred at 25° C for 16 hours. The resulting brown solution was concentrated (rotary evaporator) to ca. half volume, diluted with 20 ml. of water, and acidified to pH 3.5–4.0 with 10% hydrochloric acid. The acidified mixture was extracted with three 40-ml. portions of ether and the combined extracts were washed with two 25-ml. portions of brine, dried over magnesium sulfate, and concentrated on the rotary evaporator to leave 3.08 g. of a glass. Recrystallization from ethanol-water afforded 2.69 g. (84%) of a light yellow powder. The ir spectrum (CHCl<sub>3</sub>) showed strong absorbtions at 3.5 μ (COOH) and 5.91 μ (C=O). The nmr spectrum verified the presence of both epimers in approximately equal amounts: τ 2.2–3.0 (m, 4 H, aromatic), 3.10 (s, 1 H, C<u>H</u>=CH of one epimer), 3.08 and 3.78 (AB quartet, J = 5.5 Hz, 1 H, C<u>H</u>=C<u>H</u> of the other epimer), 7.33 (bs, 1 H, C<u>H</u>COO—), 8.33 and 8.50 (pair of s, total 3 H, (CH<sub>3</sub>)<sub>2</sub>C— of one epimer), and 8.38 and 8.47 (pair of s, total 3 H, (CH<sub>3</sub>)<sub>2</sub>C— of the other epimer).

The analytical sample was crystallized twice from ethanol-water and had m.p. 121° C. Anal. Calc'd. for $C_{14}H_{14}O_2$: C, 78.48; H, 6.59. Found: C, 79.0, 78.4; H, 6.2, 6.8. This data corresponds to that for a compound of the structure assigned to Compound (III), above.

Compound VIII; Allethrolone Ester of 2,2-Dimethyl-4,5-benzospiro[2.4]hepta-4,6-diene-1-carboxylic Acid A 25 ml. round-bottom flask containing a magnetic stirring bar was charged with 1.286 g. of the parent acid (III), above, and 10 ml. of dry benzene. To the stirring solution was added 1.5 ml. (2.24 g.) of oxalyl chloride. Considerable gas evolution was evident. The flask was topped with a drying tube and the clear, tan solution was stirred at 25°–30° C for 3 days. The reaction mixture was then concentrated on the rotary evaporator at 35° C to leave a brown oil possessing an ir band at 5.59 μ (acid chloride C=O) as the only absorbance in the carbonyl region.

The flask was flushed with argon and sealed with a rubber serum cap. A slight positive pressure of argon was maintained using an argon filled balloon; 2 ml. of dry benzene and 0.8 ml. of dry pyridine were added. After 10 min. of stirring, the mixture was cooled to 0° C and treated with 1.302 g. of allethrolone in 3 ml. of dry benzene. The reaction mixture, now tan and containing a precipitate, was stirred at 25° C for 18 hours. The reaction mixture was then poured into 30 ml. of saturated aqueous sodium bicarbonate solution and extracted with three 25-ml. portions of ether. The combined extracts were washed (brine), dried (magnesium sulfate), and concentrated (rotary evaporator) to leave 2.448 g. of a clear, tan oil. Purification of 1.005 g. of this crude product by preparative tlc on silica gel afforded 645 mg. (76%) of the pure ester (mixture of diastereomers) as a viscous yellow oil. The ir spectrum (neat film) of the product contained a strong band at 5.82 μ (ketone C=O) with a shoulder at 5.78 μ (ester C=O). The nmr spectrum (CDCl<sub>3</sub>) indicated the presence of four diastereomers: τ 2.2–3.0 (m, 4 H, aromatic), 3.15 (m, 1.5 H, C<u>H</u>=C<u>H</u>), 3.77 and 3.79 (pair of d, J = 6 Hz, total 0.5 H, —C<u>H</u>=CH on two of the diastereomers), 4.0–4.5 (bm, 2 H, C<u>H</u>=CH<sub>2</sub> and C<u>H</u>—O), 4.8–5.2 (bm, 2 H, C<u>H</u><sub>2</sub>=CH—), 7.1 (m, 2 H, C=CH—C<u>H</u><sub>2</sub>—CH=C), 7.32 and 7.34 (pair of s, total 1 H, C<u>H</u>COO—), 7.2-7.45 (m, 1 H, α to ketone), 7.58-7.95 (m, 1 H, α to ketone), 7.98, 8.02, and 8.09 (all s, total 3 H, C<u>H</u><sub>3</sub>C=C), and 8.31-8.52 (five s, total 6 H, (CH<sub>3</sub>)<sub>2</sub>C—). The ester had molecular ion m/e 348.178 (calc'd. for $C_{23}H_{24}O_3$, 348.1719). This data corresponds to that for a compound of the structure assigned to Compound (VIII), above.

EXAMPLE IV

Compound IV: 2,2-Dimethyl-4,5-benzospiro[2.4]hepta-4-ene-1-carboxylic Acid

Into a 50 ml. hydrogenation flask were placed 40 mg. of platinum oxide (Adam's catalyst), a stirring bar, and 5 ml. of ethanol. The catalyst was equilibrated with hydrogen at atmospheric pressure for 40 minutes. A sample of 429 mg. (2.0 mmole) of 2,2-dimethyl-4,5-benzospiro[2.4]hepta-4,6-diene-1-carboxylic acid (prepared as in Example III, above) in 5 ml. of ethanol was added (2 ml. ethanol rinse), stirring was started, and hydrogen consumption was measured. After 1 hour, reduction was complete (absorption of 2 mmoles of hydrogen). The reaction mixture was filtered through a pad of Celite and the filtrate was concentrated on the rotary evaporator to leave 423 mg. (98%) of a colorless solid with a melting range of 127°–145° C. The ir spectrum (CHCl<sub>3</sub>) displayed a strong band at 5.90 μ (acid C=O). The nmr spectrum (CDCl<sub>3</sub>) contained resonances at τ −0.90 (bs, 1 H, —COOH), 2.3–3.3 (m, 4 H, aromatic), 6.8–8.3 (m, 5 H, methylenes and α to COO—), and 8.43, 8.58, 8.67, and 8.80 (four s, total 6 H, (CH<sub>3</sub>)<sub>2</sub>C— for two epimers). This data corresponds to that for a compound of the structure assigned to Compound (IV), above.

Compound IX: Allethrolone Ester of 2,2-Dimethyl-4,5-benzospiro-[2.4]-hepta-4-ene-1-carboxylic Acid A dry 10 ml. round-bottomed flask with magnetic stirring bar was charged with 305 mg. of acid (IV) prepared above and 2.5 ml. of dry benzene. To this was added 0.36 ml. (0.54 g.) of oxalyl chloride. A drying tube was attached to the flask and the mixture was stirred at 25° C for 18 hours. Concentration on the rotary evaporator left an oil, the ir spectrum of which contained a band at 5.61 μ (acid chloride C=O) as the only absorbance in the carbonyl region.

The flask was flushed with argon and the reaction mixture was maintained under an inert atmosphere during the addition of 0.5 ml. of dry benzene and 0.2 ml. of dry pyridine. After 10 minutes, the solution was cooled to 0° C and treated with 307 mg. of allethrolone in 0.8 ml. of dry benzene. The turbid reaction mixture was stirred at 25° C for 3 days. The product was isolated and purified as described above for the allethrolone ester of 2,2-dimethyl-4,5-benzospiro[2.4]hepta-4,6-diene-1-carboxylic acid. The yield was 356 mg. (72%) of a pale yellow syrup. Ir analysis showed peaks at 5.78 μ (ester C=O) and 5.84 μ (cyclopentenone C=O), while the nmr spectrum displayed τ 2.3-3.2 (m, 4 H, aromatic), 4.0-4.5 (m, 2 H, C$\underline{H}$=CH$_2$ and HC-O), 4.8-5.2 (m, 2 H, HC=C$\underline{H}_2$), 6.8-7.4 (m, 4.5 H, including bisallylic and α to benzene ring), 7.67 (m, 2 H), 7.75-8.1 (m, including s at 7.99 and 8.05, total 3.5 H, including CH$_3$C=C from all diastereomers), and 8.2-9.0 (m, including at least 7 s, total 8 H, including (CH$_3$)$_2$C—). The mass spectrum showed the requisite parent ion at m/e 350. This data corresponds to that for a compound of the structure assigned to Compound (IX), above.

EXAMPLE V

Compound V;
2,2-Dimethyl-4,5,6,7-dibenzospiro[2.4]-hepta-4,6-diene-1-carboxylic Acid 9-Isopropylidenefluorene A dry 100 ml. flask with sidearm (serum cap) was charged with 3.85 g. of isopropyltriphenylphosphonium bromide. The flask was flushed with argon and, under the inert atmosphere, 40 ml. of tetrahydrofuran (freshly distilled from lithium aluminum hydride) was added. The slurry was cooled to 0° C and treated with 7.2 ml. of a 1.59 M solution of n-butyllithium in hexane. The blood red solution was stirred for several minutes at 25° C, then cooled to 0° C and treated with 1.80 g. of 9-fluorenone in 10 ml. of tetrahydrofuran. The reaction mixture was stirred at 25° C for 22 hr., concentrated to ca. 15 ml. on a rotary evaporator, and poured into 100 ml. of water. Product was extracted with four 50-ml. portions of ether. The combined extracts were washed twice (brine), dried (sodium sulfate), and concentrated to leave 4.37 g. of an oily yellow soild. Chromatography on silica gel (9:1 hexane-chloroform) gave 1.21 g. (59%) of the colorless product; m.p. 112°-113° C. The ir spectrum (CHCl$_3$) contained a strong band at 6.14 μ (C=C), while the nmr spectrum (CDCl$_3$) was virtually identical to that reported.

Ethyl 2,2-Dimethyl-4,5,6,7-dibenzospiro[2.4]hepta-4,6,-diene-1-carboxylate

A 25 ml. round-bottom three-necked flask containing a stirring bar was charged with 1.03 g. of 9-isopropylidenefluorene (prepared above) and 20 mg. of cuprous chloride. The flask was fitted with a rubber septum, a thermometer, and a reflux condenser. A slow stream of argon was maintained over the reaction mixture which was heated to 140°-150° C. To this molten material was added, dropwise via syringe, 0.55 ml. (596 mg.) of ethyl diazoacetate. At the end of the addition, heating was continued for 2 hours. After cooling, 5 ml. of diethyl ether was added and the mixture was suction filtered with generous ether washing. The filtrate was washed with 5% hydrochloric acid then with brine (twice), dried over magnesium sulfate, and concentrated to leave 1.27 g. of an oily green solid. Preparative tlc (silica gel, 2:3 hexane-chloroform R$_f$ ca. 0.4) gave 114 mg. (8%) of the product as a green solid. The nmr spectrum (CDCl$_3$) displayed τ 2.20 (bm, 3 H, aromatic), 2.72 (bm, 5 H, aromatic), 5.87 (q, J = 7 Hz, 2 H, OC$\underline{H}_2$CH$_3$), 7.22 (s, 1 H, CHCOO—), 8.30 and 8.50 (pair of s, total 6 H, (CH$_3$)$_2$C—), and 8.80 (t, J = 7 Hz, 3 H, OCH$_2$C$\underline{H}_3$).

2,2-Dimethyl-4,5,6,7-dibenzospiro[2.4]hepta-4,6-diene-1-carboxylic Acid (Compound V)

To a mixture of 114 mg. of the ethyl ester prepared above in 0.6 ml. of ethanol was added 0.9 ml. of 1.8 M aqueous potassium hydroxide. The mixture was heated at reflux for 2.5 hr., then stirred for 16 hours at 26° C. The pale green solution was diluted with 10 ml. of water, carefully acidified to pH 4 using 5% hydrochloric acid, and extracted with three 10 ml. portions of ether. The combined extracts were washed (brine), dried (magnesium sulfate), and concentrated (rotaryevaporator) to leave 100 mg. (97%) of a greenish solid. Recrystallization of 84 mg. from ethanol-water gave 65 mg. of colorless powder, m.p. > 230° C. The ir spectrum (KBr) gave typical acid bands at 3.5-4.0 μ and 5.95 μ. The nmr (CD$_3$COCD$_3$) displayed resonances at τ 2.17 (m, 3 H, aromatic), 2.65 (m, 3 H, aromatic), 7.03 (s, 1 H, CHCOO—), 8.31 (s, 3 H, CH$_3$), and 8.48 (s, 3 H, CH$_3$). This data corresponds to that for a compound of the structure assigned to Compound (V), above.

Compound X; Allethrolone Ester of 2,2-Dimethyl-4,5,6,7-dibenzospiro[2.4]hepta-4,6-diene-1-carboxylic Acid To 55 mg. of acid V, prepared above, in a 5 ml. round-bottom flask with a magnetic stirring bar were added 0.40 ml. of dry benzene, then 54 μl. (80 mg.) of oxalyl chloride. The reaction flask was stoppered and the mixture was stirred at 25° C for 18 hours. Concentration of the clear yellow solution left 57 mg. of a low melting solid, the ir spectrum of which exhibited a band at 5.57 μ (acid chloride C=O) as the only absorbance in the carbonyl region.

To the acid chloride under a blanket of argon were added 0.3 ml. of dry benzene and 30 μl. of dry pyridine. After stirring 10 minutes, the mixture was cooled to 0° C and 43 μl. (46 mg.) of allethrolone was added. The resulting slurry was stirred at 25° C for 3 days. Product isolation and purification as described for the above allethronyl spiro esters afforded 48 mg. (57%) of product. The ir spectrum displayed bands at 5.78 (ester C=O) and 5.82 μ (cyclopentenone C=O); the nmr spectrum showed τ 2.2 (m, 3 H, aromatic), 2.7 (m, 5 H, aromatic), 4.0-4.6 (m, 2 H, C$\underline{H}$=CH$_2$ and HC-O), 4.8-5.3 (m, 2 H CH=C$\underline{H}_2$), 7.1 (m, 2 H, C=C-CH$_2$-C=C), 7.20 (s, 1 H, CH-COO—), 7.1-8.2 (series of m, 2 H, —CH$_2$-C=O), 7.97 (s, 1.5 H, CH$_3$C=C of one diastereomer), 8.33 (s, 1.5 H, CH$_3$C=C of the other diastereomer), and 8.27 and 8.47 (pair of s, total 6 H, (CH$_3$)$_2$C—). The data corresponds to that for a compound of the structure assigned to Compound (X), above.

EXAMPLE VI

Insecticidal compositions comprising the allethrolone esters VI through IX, above, dissolved in 5 ml. acetone and dispersed in distilled water with 500 ppm Span 85 and 125 ppm Tween 80 emulsifiers(fatty acid esters and polyethylene oxide esters of sorbitan mono-oleate) were prepared and tested. Similar compositions containing allethrin were used as controls. Compound X was dissolved in kerosene and sprayed on the test insects. The sprays were applied from a Waters vertical spray tower operating at 10 p.s.i. and discharging about 30 ml. of material per minute through an atomizer. The spray descends through an 8 inch stainless steel cylinder to plant material and/or test insects 44 inches below the atomizer. The insects were retained for knockdown and/or mortality observations. Test compositions having the indicated percentage concentration of test compounds were utilized in the tests. The housefly results are set forth in Table 1 below and demonstrate the superior insecticidal activity of these compounds. The data in Table 2 demonstrate the superior insecticidal activity of these compounds against a variety of other insects.

Table 1
Houseflies
| Concentration (Wt.) | (VI) 2 hr. Knock-down | (VI) 24 hr. Kill | (VII) 2 hr. Knock-down | (VII) 24 hr. Kill | (VIII) 2 hr. Knock-down | (VIII) 24 hr. Kill | (IX) 2 hr. Knock-down | (IX) 24 hr. Kill | (X) 2 hr. Knock-down | (X) 24 hr. Kill | 2 hr. Knock-down | 24 hr. Kill |
|---|---|---|---|---|---|---|---|---|---|---|---|---|
| .1 | 100 | 48 | 100 | 100 | 100 | 100 | 100 | 100 | 23 | 15 | 100 | 100 |
| .05 | — | — | — | — | 100 | 100 | 94 | 94 | 19 | 19 | 100 | 100 |
| .01 | 0 | 0 | 14 | 18 | 20 | 0 | 90 | 80 | — | — | 80 | 39 |
| .01/0.04 | — | — | — | — | 100 | 92 | — | — | — | — | — | — |
| .005/0.1 | 100 | 87 | 96 | 99 | — | — | — | — | 37 | 31 | — | — |
| .005/0.02 | — | — | — | — | — | — | — | — | — | — | — | — |
| .0025/0.025 | 2 | 0 | 0 | 2 | — | 0 | 0 | 0 | — | — | — | — |
*R = 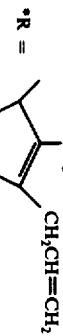
** Conc. ester/piperonyl butoxide synergist
— = No test data Table 2

| Concentration (Wt.) | ![structure 1: cyclopentadiene with CH3, CH3, COOR*] | | | ![structure 2: spiro cyclopentane cyclopropane with CH3, CH3, COOR*] | | | ![structure 3: indene-fused cyclopropane with CH3, CH3, COOR*] | | | ![structure 4: indane-fused cyclopropane with CH3, CH3, COOR*] | | | ![structure 5 (Allethrin): CH3, CH3, CH3, COOR] | | |
|---|---|---|---|---|---|---|---|---|---|---|---|---|---|---|---|
| | S. Army-worm | Mex. Bean Beetle | Pea Aphid | S. Army-worm | Mex. Bean Beetle | Pea Aphid | S. Army-worm | Mex. Bean Beetle | Pea Aphid | S. Army-worm | Mex. Bean Beetle | Pea Aphid | S. Army-worm | Mex. Bean Beetle | Pea Aphid |
| 0.10 | 30 | 100 | 30 | 80 | 100 | 100 | 90 | 100 | 100 | 40 | 100 | 100 | 100 | 100 | 100 |
| 0.05 | — | — | — | 30 | 100 | 100 | — | — | — | — | — | — | — | — | — |
| **0.05/0.2 | — | — | — | 50 | 100 | — | 60 | 90 | 80 | 20 | 100 | — | — | — | — |
| 0.01 | — | — | — | 0 | 60 | 0 | — | 10 | 10 | — | 90 | 60 | <10 | 90 | 70 |
| **0.01/0.04 | — | — | — | 0 | 70 | 90 | 80 | 100 | 100 | 0 | 80 | 80 | 90 | 100 | 50 |
| 0.005 | — | — | — | — | — | — | 10 | 70 | 80 | — | 60 | 30 | — | 90 | 50 |
| **0.005/0.02 | — | — | — | — | — | — | — | — | — | — | — | — | 20 | 100 | 100 |
| **0.0025/0.01 | — | — | — | — | — | — | — | — | — | — | — | — | — | 60 | 90 |
| **0.001/0.004 | — | — | — | — | — | — | — | — | — | — | — | — | — | — | — |

*R = CH₂CH=CH₂ on cyclopentanone with CH₃

** Conc. ester/piperonyl butoxide synergist
— = No test data

In another series of tests, the allethrolone esters of the spiro carboxylic acids (II) and (III), above, were applied to strawberry spider mites and exhibited significant miticidal activity.

Esters (VI) through (X) of the instant invention are insecticidally effective when tested against a wide variety of insects including the Southern army worm, the Mexican bean bettle, the pea aphid, the mite, the German cockroach, the adult mosquito, adult stable flies, black carpet beetle larva, webbing clothes moth larva, adult rice weevils, and adult sawtooth grain beetles.

Insecticidal and miticidal compositions containing the esters of the present invention can be formulated and utilized as oil solutions, emulsifiable concentrates, wettable powders, dusts, aerosols, or impregnated into wood, fabrics, etc., and provide a long lasting residual effect. Such compositions can include the generally employed inert carriers or diluents and auxiliary agents which are well-known to those skilled in the art. (By "inert" herein is meant carriers which, themselves, have no substantial insecticidal activity.) For example, suitable dusts can be prepared by admixing the compounds of the invention with dry free-flowing powders such as clay, bentonite, fuller's earth, diatomaceous earth, pyrophyllite, attapulgite, calcium carbonate, chalk and the like. The active compounds of the invention normally comprise up to about 10% by weight of such dust formulations. An amount of up to about 3% is preferred and is suitable for most applications.

Liquid insecticidal and miticidal compositions herein comprise an insecticidal amount, i.e., from about 0.1% to about 20%, preferably 1% to about 10% by weight, of one or more of the esters (VI) through (X), above.

Liquid suspensions or dispersions of the esters in a non-solvent carrier liquid, such as water, can be suitably employed for the treatment of foliage. Also suitably employed are solutions of the present insecticidal esters in oil which is emulsified in water. Examples of oil solvents include hydrocarbons such as benzene and toluene, halogenated hydrocarbons such as chlorobenzene, chloroform, fluorotrichloromethane and dichlorodifluoromethane, and commercial mixtures of hydrocarbons such as the common Stoddard solvents, petroleum ethers, and the like.

Aerosols can be prepared by dissolving the esters of this invention in a highly volatile liquid carrier such as trifluorochloromethane, nitromethane, dichlorodifluoroethane and the like, or by dissolving such compounds in a less volatile carrier, such as benzene or kerosene, and admixing the resulting solution with a highly volatile liquid aerosol propellant such as the polyfluorohydrocarbons commonly used in aerosol insecticide formulations.

The novel esters of the invention are useful for destroying a variety of insects and mites. Accordingly, a method aspect of the present invention comprises combating insects by applying to insects (including mites) or to an insect habitat one or more of novel esters (VI through X, above) of the invention. For broad scale applications, the esters herein are applied at a rate of from about 0.5 to about 10 pounds per acre.

Preferably the esters of this invention are employed in combination with a synergistic agent, for example, piperonyl butoxide, sulfoxide, $\beta$-butoxy$\beta'$-thiocyanodiethyl ether and like.

What is claimed is:

1. 2,2-dimethyl-4,5-benzospiro[2.4]hepta-4,6-diene-1-carboxylic acid.
2. 2,2-dimethyl-4,5-benzospiro[2.4]hepta-4-ene-1-carboxylic acid.
3. The allethrolone ester of the acid of claim 1.
4. The allethrolone ester of the acid of claim 2.
5. The allethrolone ester of 2,2-dimethyl-4,5,6,7-dibenzospiro[2,4]-hepta-4,6-diene-1-carboxylic acid.

* * * * *